United States Patent [19]
Rosenbaum et al.

[11] Patent Number: 4,750,908
[45] Date of Patent: Jun. 14, 1988

[54] COMPOSITION AND METHOD FOR DYEING HUMAN HAIR WITH ISATIN

[75] Inventors: Gorges Rosenbaum, Asnieres; Jean Cotteret, Limay, both of France

[73] Assignee: L'Oreal, Paris, France

[21] Appl. No.: 919,491

[22] Filed: Oct. 16, 1986

[30] Foreign Application Priority Data

Oct. 16, 1985 [FR] France ................... 85 15311

[51] Int. Cl.⁴ ............................................. A61K 7/13
[52] U.S. Cl. .................................. 8/429; 8/405; 8/435; 548/485
[58] Field of Search .................. 548/485; 8/405, 404, 8/429, 435

[56] References Cited

U.S. PATENT DOCUMENTS 3,446,817  5/1969  Harvey et al. ............ 548/485
4,188,325  2/1980  Gassman et al. .......... 548/485

FOREIGN PATENT DOCUMENTS 2716671  10/1978  Fed. Rep. of Germany .
2119411  11/1983  United Kingdom .

OTHER PUBLICATIONS

Venkataraman, *The Chemistry of Synthetic Dyes*, vol. 5, pp. 475–478, Academic Press, N.Y., 1971.

Heller, "Color Phenomena of Alkaline Isatin Solution", *Chemical Abstracts*, 1:1703, 1906.
Marchlewski et al., "Absorption of Violet Light by Organic Substances", *Chemical Abstracts*, 19:1663, 1925.
Hibbert, "Effect of Light on Colored Fabric", *Chemical Abstracts*, 23:280, 1929.
Venkataraman, "The Chemistry of Synthetic Dyes, vol. 2, pp. 1003–1007; 1022–1026, Academic Press, N.Y., 1952.
"Beilsteins Handbuch der Organischen Chemie", 4th Edition, vol. 21, Hauptwerk, 1935, pp. 432–435.
Seifen-Öle-Fette-Wachse, vol. 98, No. 16, 1972, p. 512.

*Primary Examiner*—Paul Lieberman
*Assistant Examiner*—Linda D. Skaling
*Attorney, Agent, or Firm*—Fleit, Jacobson, Cohn & Price

[57] ABSTRACT

The invention relates to the use of 2,3-indolinedione of formula:

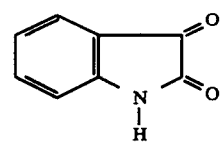

for dyeing keratinous fibres, especially human hair.

12 Claims, No Drawings

COMPOSITION AND METHOD FOR DYEING HUMAN HAIR WITH ISATIN

The present invention relates to the use of 2,3-indolinedione, also known as "isatin", for dyeing keratinous fibres, especially human hair.

In the direct dyeing of hair, that is when the dye is not developed by oxidation, many classes of dyes are used, such as nitro dyes of the benzene series, triarylmethane dyes, indoamine dyes and azo dyes.

These dyes, as is well known, are generally used mixed in order to obtain natural tints.

To this end, yellow or green-yellow dyes are sought in order to produce shades having natural glints, in particular when these dyes are combined with blue or violet dyes and orange dyes, to provide a golden shade.

We have discovered that isatin, which is known per se, possesses advantageous dyeing properties for keratinous fibres, and more especially hair, in particular in formulations in which it is one of the basic constituent yellow dyes.

Accordingly the present invention provides a composition suitable for direct dyeing of keratinous fibres comprising 2,3-indolinedione of formula:

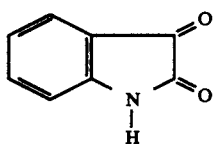

(I)

and a cosmetically acceptable diluent, the composition being in the form of an anhydrous liquid, a thickened liquid, a cream, an aqueous or anhydrous gel, an oil, or a powder.

By the words "a composition suitable for direct dyeing" we mean a composition which can be used for dyeing keratinous fibres either as it is or after mixture with water or another diluent.

This dye is especially advantageous when it is combined with quinone dyes of the benzoquinone or hydroxynaphthoquinone family which are described, inter alia, in French Patents Nos.2,517,199 and 2,517,200, and in French Patent Application Publication No.2,537,433.

We have discovered, moreover, that an especially advantageous embodiment is its use in anhydrous dyeing compositions of the type described in French Patent Application Publication No.2,526,031.

In this medium isatin possesses good solubility, good dyeing power, regardless of the proportions of surfactant and especially nonionic surfactant present, and good stability.

Isatin can be used for the direct dyeing of keratinous fibres, especially human hair, that is to say without employing an oxidation process, in amounts which are effective for dyeing the fibres. These amounts are preferably from 0.05 to 15% by weight relative to the total weight of the composition in which it is employed.

According to an especially preferred embodiment, isatin is used in combination with quinone dyes. Examples of these dyes are:

2-hydroxynaphthoquinones of formula:

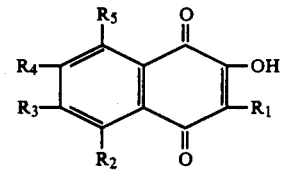

(II)

in which $R_1$ denotes a hydrogen or halogen atom, or a hydroxyl, alkoxy, nitro, alkyl or acyl group, and $R_2$, $R_3$, $R_4$ and $R_5$ each denote, independently of each other, a hydrogen atom, or a hydroxyl, alkoxy, alkyl or acyl group. The alkoxy and alkyl groups preferably have from 1 to 4 carbon atoms, and the acyl groups preferably have from 2 to 4 carbon atoms. Among these compounds, lawsone, naphthazarin and 2-hydroxynaphthoquinones described in French Patent No.2,517,199 may especially be mentioned;

benzoquinones of formula:

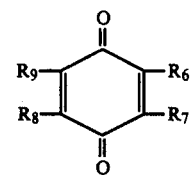

(III)

in which $R_6$ and $R_8$ each denote, independently of each other, a hydrogen atom, or a hydroxyl, alkoxy or optionally hydroxylated alkyl group, and $R_7$ and $R_9$ each denote, independently of each other, a hydrogen atom, or a hydroxyl, alkoxy, alkyl having 1 to 3 carbon atoms, or phenyl, optionally substituted with OH, group, these compounds having at most two alkyl or alkoxy groups on the quinone ring. These compounds are described in French Patent 2,517,200.

5-hydroxynaphthoquinones of formula:

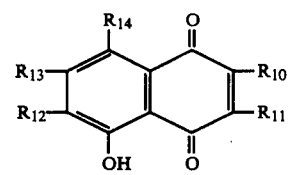

(IV)

in which $R_{10}$ and $R_{11}$ each denote, independently of each other, a hydrogen or halogen atom, or a methyl, methoxy or nitro group, $R_{12}$ and $R_{13}$ each denote, independently of each other, a hydrogen atom, or a hydroxyl, methyl or methoxy group, and $R_{14}$ denotes a hydrogen atom or a methyl or methoxy group. Among these compounds, juglone and 5-hydroxynaphthoquinones described in French Patent Application Publication No.2,537,433 may especially be mentioned.

Istain is preferably employed in dyeing compositions containing, in a medium suitable for dyeing keratin fibres, especially hair, for example hair on the head, the dye optionally with at least one other dye which is a nitro dye of the benzene series or an azo, triarylmethane or indoamine dye or any other direct dye. Especially preferred dyes are the quinone dyes mentioned above.

An especially preferred composition comprises isatin and 2,5-dihydroxy-3-methyl-6-methoxy-1,4-benzoquinone, 3-methyl-2-hydroxy-1,4-naphthoquinone, 3-methoxy-2-hydroxy-1,4-naphthoquinone, 2,3-dihydroxy-1,4-napththoquinone and/or 2,5-dihydroxy-3,6-dimethoxy-1,4-benzoquinone.

The dyes other than isatin preferably represent from 0.005 to 10% by weight of the total weight of the composition.

The compositions which can be used according to the invention are preferably aqueous or anhydrous liquid compositions which may be thickened to a greater or lesser extent, or are creams, aqueous or anhydrous gels, oils, or powders, also known as "cataplasms", which are diluted with a liquid at the time of use.

In a first preferred embodiment of the invention, the suitable cosmetic medium is aqueous and has a pH of from to 11, preferably from 2 to 7, the pH being adjusted to the desired value using known alkalinizing or known acidifying agents.

These compositions can contain anionic, cationic, nonionic or amphoteric surfactants, or mixtures thereof. Examples of suitable surfactants are soaps, alkylbenzenesulphonates, alkylnaphthalenesulphonates, sulphates or ether sulphates or sulphonates of fatty alcohols, quaternary ammonium salts, fatty acid diethanolamides, polyoxyethyleneated or polyglycerolated acids or alcohols or amides, and polyoxyethyleneated or polyglycerolated alkylphenols. These surfactants are preferably present in the compositions according to the invention in a proportion of from 0.1 to 55% by weight, and preferably from 1 to 40% by weight, relative to the total weight of the composition.

The aqueous compositions may contain an organic solvent, for example lower alkanols such as ethanol or isopropanol, polyols such as glycerol, glycols or glycol ethers such as ethylene glycol, propylene glycol, ethylene glycol monobutyl ether, or diethylene glycol monoethyl ether or monomethyl ether, or mixtures thereof.

These solvents are preferably used in a proportion of from 1 to 60% by weight, and more especially from 3 to 30% by weight, relative to the total weight of the composition.

These compositions may also contain anionic, nonionic, cationic or amphoteric polymers, or mixtures thereof, preferably in a proportion of from 0.1 to 5% by weight relative to the total weight of the composition.

These compositions may be thickened with thickening agents, for example sodium alginate, gum arabic, guar or carob gum, xanthan gum, pectins, cellulose derivative such as methylcellulose and hydroxymethylcellulose, hydroxypropylcellulose and carboxymethylcellulose, and various polymers having a thickening function such as acrylic acid derivatives. Inorganic thickening agents such as bentonite may also be used.

These thickening agents are preferably present in a proportion of from 0.1 to 5% by weight, especially from 0.5 to 3% by weight, relative to the total weight of the composition.

These compositions may also contain any other adjuvant customarily used in compositions for hair dyeing, such as penetrants, sequestering agents, antioxidants, buffers and perfumes.

A preferred medium is the anhydrous medium described in French Patent Application Publication No.2,526,031.

An "anhydrous medium" is understood to mean a medium which does not contain more than 1% water.

The anhydrous medium comprises, according to a preferred variant of the invention, a mixture of at least one anhydrous solvent and one or more anhydrous surfactants, such that the composition preferably contains at least 15% solvent and at least 20% surfactant.

The solvents used are those which are cosmetically acceptable, for example saturated $C_2$–$C_{20}$ monohydric alcohols such as ethanol, isopropanol, cetyl alcohol or octyldodecanol; polyols such as alkylene glycols, for example ethylene glycol, propylene glycol, glycerol or diethylene glycol; glycol ethers such as mono-, di- and triethylene glycol monoalkyl ethers, for example ethylene glycol monoethyl ether, ethylene glycol monobutyl ether or diethylene glycol monoethyl ether; esters such as, for example, ethylene glycol monomethyl ether acetate or ethylene glycol monoethyl ether acetate; and esters of saturated lower alcohols and fatty acids, such as isopropyl myristate or palmitate.

The term "lower" is generally intended to mean from 1 to 6 carbon atoms and preferably from 1 to 4 carbon atoms.

The especially preferred solvents are ethanol, cetyl alcohol, propylene glycol, ethylene glycol monoethyl ether and ethylene glycol monobutyl ether.

The surfactants used in this embodiment are preferably anhydrous surfactants of the anionic, nonionic, cationic or amphoteric type, preferably the nonionic type, or mixtures thereof. Examples of these are polyoxyethyleneated fatty alcohols, polyoxyethyleneated alkylphenols or naphthols, monoalkyltrimethylammonium halides, dialkyldimethylammonium halides, soaps and polyglycerolated fatty alcohols.

The compositions can contain an anhydrous alkalinizing or acidifying agent such as, for example, citric acid, ascorbic acid, acetic acid, lactic acid or an alkanolamine such as those which are fully substituted on the amine group, for example dimethylamino ethanol.

The anhydrous compositions according to the invention may also contain various additives which are usable in cosmetics, with the single proviso that they contain less than 1% of water. Various additives which can be used include perfumes, sequestering agents, thickening agents, treatment agents, antioxidants, vegetable or mineral oils, preservatives and organic salts.

In this embodiment, isatin is preferably used together with 3-methyl-6-methoxy-2,5-dihydroxybenzoquinone, 2,5-dihydroxy-1,4-naphthoquinone, 3-methyl-2,5-dihydroxy-1,4-naphthoquinone, 3-methoxy-2-hydroxy-1,4-naphthoquinone, 2-methyl-3,5-dihydroxy-1,4-naphthoquinone, lawsone and/or 2,3-dihydroxy-1,4-naphthoquinone.

The compositions may be applied as they are on wet hair, or can be diluted immediately before use. In the latter case the compositions according to the invention are diluted at the time of dyeing with an aqueous solution such that the ratio of the composition according to the invention to the aqueous solution is from 0.25:1 to 2:1. The aqueous solution may consist of pure water, but can also comprise any other complex aqueous liquid, thickened to a greater or lesser extent, such as a carrier customarily used in dyeing compositions for hair.

In this case, the components of the cosmetic medium can be all types of cosmetically acceptable ingredients, anhydrous or otherwise, which are customarily used in this type of composition.

Isatin can also be used in the form of a cataplasm, that is to say in the form of a powder to be diluted with a liquid at the time of use.

In this embodiment, isatin and optionally other dyes chosen are prepared in the form of a powder which is stable on storage and are introduced into a solid medium which can consist of powders, flours or amylaceous or mucilagineous substances which are diluted at the time of use with an appropriate liquid so as to form a mixture which has a suitable consistency for application to the keratin fibres. The powders or flours used in this type of composition generally consist of substances which are insoluble in aqueous media, such as silicas, clays or plants which are powdered before or after extraction of their active principles by solvents.

In this embodiment isatin is preferably used with juglone, lawsone, 2,5,8-trihydroxy-1,4-naphthoquinone, 5,8-dihydroxy-1,4-naphthoquinone, 2-methyl-5-hydroxy-1,4-naphthoquinone, 2,5,7-trihydroxy-1,4-naphthoquinone, 3-methyl-2,5-dihydroxybenzoquinone, 3-methyl-6-methoxy-2,5-dihydroxybenzoquinone, 2,5-dihydroxy-1,4-naphthoquinone, 3-methyl-2,5-dihydroxy-1,4-naphthoquinone, 3-methoxy-2-hydroxy-1,4-naphthoquinone, 2-methyl-3,5-dihydroxy-1,4-naphthoquinone and/or 2,3-dihydroxy-1,4-naphthoquinone.

The liquid can comprise water, or water with cosmetically acceptable solvents such as an alcohol, glycol or oil.

The liquid medium is preferably added to the powder in a proportion such that, after mixing, a paste is obtained having a viscosity of from 0.3 to 5 Pa.s.

The process according to the invention for dyeing keratinous fibres, and especially human hair, comprises applying isatin, preferably in the form of a dyeing composition of the type described above, to the fibres and preferably to hair before or after shampooing.

The composition is preferably left in place for from 1 to 60 minutes, preferably from 1 to 40 minutes, and the fibres are then rinsed and dried.

Isatin may also be applied, after shampooing, in a hair setting composition which may contain a polymer customarily used for this type of treatment, this application being followed by drying.

One of the forms of application of the present invention consists in diluting a powder containing isatin at the time of use with a liquid as defined above, applying the resulting cataplasm to the fibres and, after an exposure time of from 1 to 40 minutes, rinsing the hair as described above. The cataplasm preferably has a viscosity of from 300 to 5,000 centipoises.

The examples which follow illustrate the invention.

Example 1

The following composition is prepared:

| | |
|---|---|
| 2,3-Indolinedione | 1.5 g |
| 2-Hydroxy-3-methyl-1,4-naphthoquinone | 1 g |
| Citric acid | 1 g |
| Anhydrous ethyl alcohol | 28.5 g |
| Oxyethyleneated nonylphenol containing g moles of ethylene oxide, sold by HENKEL under the name SINNOPAL NP 9 | qs 100 g |

At the time of use, this liquid is diluted with 1.5 times its weight of water. A gel is obtained which is applied for 20 minutes on dark blond hair.

After being rinsed and dried, the hair shows a slightly coppery golden glint.

Example 2

The following composition is prepared:

| | |
|---|---|
| 2,3-Indolinedione | 0.8 g |

-continued

| | |
|---|---|
| 2,5-Dihydroxy-3-methyl-6-methoxy-1,4-benzoquinone | 0.2 g |
| 2-Hydroxy-3-methyl-1,4-naphthoquinone | 0.4 g |
| 2,3-Dihydroxy-1,4-naphthoquinone | 0.15 g |
| Dialkyldimethylammonium chloride, sold by HOECHST under the name GENAMIN DSAC | 1 g |
| Anhydrous ethyl alcohol | 30 g |
| Citric acid | 1 g |
| Oxyethyleneated nonylphenol containing 9 moles of ethylene oxide, sold by HENKEL under the name SINNOPAL NP 9 | qs 100 g |

After the head of blond hair has been well moistened, this foaming liquid is applied to it for 20 minutes.

After rinsing and drying, a pearlybeighe glint is obtained.

Example 3

The following composition is prepared:

| | |
|---|---|
| 2,3-Indolinedione | 8 g |
| Red sandalwood dust of particle size less than or equal to 130 μm | 45 g |
| Powdered residue of exhaustive extraction of soapwort, of particle size less than or equal to 90 μm | 23 g |
| Citric acid | 5 g |
| Polysaccharide derived from carob seed, sold by UNIPECTINE under the name VIDOGUM L 175 | 2.5 g |
| Glucose | qs 100 g |

Before use, this powder is made into a paste with twice its weight of water at 41° C.

The mixture obtained is applied in the form of a cataplasm for 30 minutes on light blond hair.

The hair is rinsed and dried.

The glint obtained is a golden glint.

Example 4

The following composition is prepared:

| | |
|---|---|
| 2,3-Indolinedione | 1 g |
| 2-Methoxy-5-hydroxy-1,4-naphthoquinone | 0.3 g |
| 2,5-Dihydroxy-1,4-naphthoquinone | 1 g |
| Citric acid | 1 g |
| Cetyl alcohol | 24 g |
| Cetyl/stearyl alcohol containing 15 moles of ethylene oxide, sold by HENKEL under the name MERGITAL CS 15E | 23 g |
| Octyldodecanol | qs 100 g |

This cream is diluted at th e time of use with its own weight of cold water. The creamy mixture is applied on chestnut-brown hair for 30 minutes. The air then rinsed and dried.

A coppery glint is obtained.

Example 5

The following composition is prepared:

| | |
|---|---|
| 2,3-Indolinedione | 0.5 g |
| Vinyl acetate/crotonic acid (90:10) copolymer | 1.8 g |
| Vinylpyrrolidone/vinyl acetate (60:40) copolymer | 0.4 g |
| Ethyl alcohol | qs 50° alcoholic strength |
| Triethanolamine | qs pH 6 |

This hair setting lotion, applied without rinsing on blond hair, endows it with a matt golden glint.

Examaple 6

The following composition is prepared:

| | |
|---|---|
| 2,3-Indolinedione | 0.25 g |
| 2-(β-Hydroxyethyl)amino-5-hydroxy-1-nitrobenzene | 0.15 g |
| 2-(β-Hydroxyethyl)amino-5-bis(β-hydroxyethyl)amino-1-nitrobenzene | 0.3 g |
| Sodium alkyl ether sulphate containing 0.6 meq/g, sold under the name SACTIPON 8533 by LEVER | 20 g |
| Ethylene glycol monoethyl ether | 10 g |
| Lactic acid | qs pH 5 |
| Demineralized water | qs 100 g |

This dyeing shampoo, applied for 20 minutes on light chestnut-coloured hair, endows it, after rinsing and drying, with a coppery dark auburn glint.

We claim:

1. A composition suitable for direct dyeing of human hair comprising 2, 3-indoline dione of formula

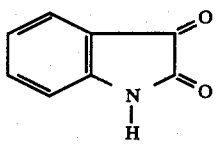

(I)

in an amount of 0.05 to 15% by weight, and a cosmetically acceptable medium, said medium being (i) aqueous and having a pH from 2 to 11, and further containing one of the following: an anionic, cationic, non ionic or amphoteric surfactant or mixtures thereof, an anionic, non ionic, cationic or amphoteric polymer, or mixtures thereof, a thickening agent, a penetrant, a sequestering agent, an antioxidant, or a perfume, (ii) an anhydrous gel, (iii) an oil, or (iv) a powder.

2. A composition according to claim 1 in which the anhydrous gel, or the oil, further contains one of the following: an anionic, cationic, non ionic or amphoteric surfactant or mixtures thereof, an organic solvent, an anionic, non ionic, cationic or amphoteric polymer, or mixtures of said polymers, a thickening agent, a penetrant, a sequestering agent, an antioxidant, or a perfume.

3. A composition suitable for direct dyeing of human hair which is anhydrous and which comprises at least 15% by weight relative to the total weight of the composition of at least one anhydrous solvent, and at least 20% by weight relative to the total weight of the composition of at least one anhydrous surfactant, and 0.05 to 15% by weight of the 2,3-indoline dione of formula:

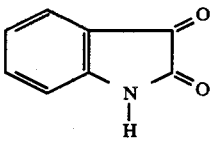

(I)

4. A composition according to claim 3 wherein the anhydrous solvent is a saturated lower monohydric alcohol, a saturated long-chain monohydric alcohol, a polyol, a glycol ether, a glycol ester, or an ester of a fatty acid and a lower alcohol.

5. A composition according to claim 1 which is in the form of a powder intended to be diluted with a liquid at the time of use, wherein the cosmetically acceptable medium comprises a solid medium consisting of an amylaceous or mucilagineous substance, a silica, clay, or a plant powdered before or after extraction of an active principle by a solvent.

6. A composition according to claim 1 which additionally comprises, as a further direct dye, a nitro dye of the benzene series, an azo dye, a triarylmethane dye, an indoamine dye or a quinone dye.

7. A composition according to claim 6 which comprises a 2-hydroxynapthoquinone dye of formula:

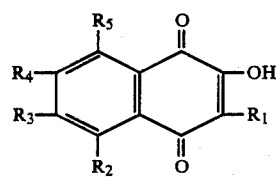

(II)

in which $R_1$ denotes a hydroen or halogen atom, or a hydroxyl, $C_1$–$C_4$ alkoxy, niro, $C_1$–$C_4$ alkyl or $C_2$–$C_4$ acyl group, and $R_2$, $R_3$, $R_4$ and $R_5$ each denote, independently of each other, a hydrogen atom, or a hydroxyl, $C_1$–$C_4$ alkoxy, $C_1$–$C_4$ alkyl or $C_2$–$C_4$ acyl group; or a benzoquinone dye of formula:

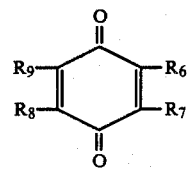

(III)

in which $R_6$ and $R_8$ each denote, independently of each other, a hydrogen atom, or a hydroxyl, alkoxy, alkyl or hydroxylated alkyl group, and $R_7$ and $R_9$ each denote, independently of each other, a hydrogen atom, or a hydroxyl, alkoxy, alkyl having 1 to 3 carbon atoms, phenyl or phenyl substituted with OH group, these compounds having at most two alkyl or alkoxy groups on the quinone ring; or a 5-hydroxynapthoquinone dye of formula:

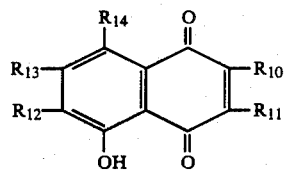

(IV)

in which $R_{10}$ and $R_{11}$ eaoh denote, independently of each other, a hydrogen or halogen atom, or a methyl, methoxy or nitro group, $R_{12}$ and $R_{13}$ each deote, independently of each other, a hydrogen atom, or a hydroxyl, methyl or methoxy group, and $R_{14}$ denotes a hydrogen atom or a methyl or methoxy group.

8. A composition according to claim 6 which comprises from 0.005 to 10% by weight direct dyes other than 2,3-indolinedione relative to the total weight of the composition.

9. A process for direct dyeing of human hair which comprises applying to the hair a composition comprising a tinctorially effective amount of a 2, 3-idoline dione of formula:

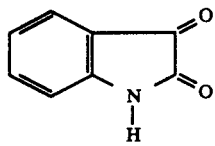
(I)

in a cosmetically acceptable medium, leaving the composition in place for from 1 to 60 minutes, and rinsing and drying the hair.

10. A process according to claim 9 wherein the composition comprises, in addition to the dye, an anionic, cationic, nonionic or amphoteric polymer, or mixture thereof and wherein a hair setting process is carried out simultaneously with the dyeing process.

11. A process according to claim 9 wherein the composition comprises a cataplasm obtained by adding a cosmetically acceptable liquid to a powder containing the dye in a proportion sufficient to obtain a viscosity of from 0.3 to 5 Pa.s.

12. A process according to claim 9 wherein the composition further comprises a quinone dye.

* * * * *